United States Patent [19]

Tomlinson

[11] Patent Number: 4,981,678

[45] Date of Patent: Jan. 1, 1991

[54] FOAMABLE BIOCIDE COMPOSITION

[75] Inventor: Roderick P. J. Tomlinson, Victoria, Australia

[73] Assignee: Soltec Research Pty., Ltd., Scoresby, Australia

[21] Appl. No.: 494,228

[22] Filed: Mar. 15, 1990

Related U.S. Application Data

[60] Division of Ser. No. 277,262, Nov. 29, 1988, Pat. No. 4,915,934, which is a continuation-in-part of Ser. No. 17,817, Feb. 24, 1987, abandoned, which is a continuation-in-part of Ser. No. 758,558, Jun. 18, 1985, abandoned.

[30] Foreign Application Priority Data

Oct. 24, 1983 [AU] Australia .................. PG2011/83

[51] Int. Cl.$^5$ .................................................. A61K 9/12
[52] U.S. Cl. ........................................ 424/45; 514/945
[58] Field of Search .............................................. 424/45

[56] References Cited

U.S. PATENT DOCUMENTS

| | | | |
|---|---|---|---|
| 3,584,115 | 6/1971 | Gebhart et al. | 424/45 |
| 3,787,566 | 1/1974 | Gauvreau | 424/45 |
| 3,949,066 | 4/1976 | Clark | 424/47 |
| 4,199,567 | 4/1980 | Rankin | 514/635 |
| 4,347,154 | 8/1982 | Simmens | 424/45 |
| 4,534,958 | 8/1985 | Adams et al. | 424/45 |
| 4,548,807 | 10/1985 | Westfall et al. | 424/45 |
| 4,716,032 | 12/1987 | Westfall et al. | 424/45 |
| 4,795,761 | 1/1989 | Curtis-Prior | 514/843 |
| 4,801,444 | 1/1989 | Kravchenko | 424/45 |
| 4,834,969 | 5/1989 | Grollier | 424/45 |
| 4,915,934 | 4/1990 | Tomlinson | 424/45 |

FOREIGN PATENT DOCUMENTS

| | | | |
|---|---|---|---|
| 1157758 | 2/1952 | Australia . | |
| 222033 | 6/1957 | Australia | 9.6/87.1 |
| 463216 | 11/1973 | Australia | 424/45 |
| 1120860 | 3/1982 | Canada | 424/45 |
| 2576180 | 7/1986 | France . | |

OTHER PUBLICATIONS

Lilly et al., publication entitled "Detergents Compared with Each Other and with Antiseptics as Skin 'Degerming' Agents", p. 91.

Chester et al., publication entitled "Skincare and the Aerosol Mousse", dated Dec. 1985.

Daly, Jr., publication entitled, "A New Era in Aerosol Propellants", dated Feb. 1984, p. 40.

Pettoruto, U.S. Defensive Publication No. 943,010 entitled "Foamable Chlorhexidine-Containing System"; 1975.

Brahic, CA 106: 28859t (1986), of FR. 2576180, 25 Jul. 1986.

Pettoruto, CA 85: 25400q (1976), of USPTO T 943010, 3 Feb. 976.

Tomlinson, CA 103: 76775j (1985), PCT WO 85/1876, 9 May 1985.

*Primary Examiner*—Shep K. Rose
*Attorney, Agent, or Firm*—Benasutti

[57] ABSTRACT

A boicidal composition made up of an alcholic chlorhexidine solution; from 0.1 to 20% w/w of a quick breaking foaming agent; from 3 to 30% w/w of an aerosol propellant; and optionally, a corrosion inhibitor.

6 Claims, No Drawings

FOAMABLE BIOCIDE COMPOSITION

This is a divisional of copending application Ser. No. 07/277,262 filed on Nov. 29, 1988 now U.S. Pat. No. 4,915,734 which is a continuation-in-part of application Ser. No. 07/017,817, filed on Feb. 24, 1987, now abandoned, which is a continuation-in-part of application Ser. No. 06/758,558, filed on June 18, 1985, now abandoned, all of which are hereby incorporated by reference.

BACKGROUND OF THE INVENTION

The present invention relates to a foamable biocidal composition.

The chemical control of bacteria and viruses is assuming increasing importance in the hosiptal and medical environment. Outbreaks of infections such as Methyicylin resistant Staph Aureus are causing illness, death and even temporary closure of wards in some hospitals.

This situation has been exacerbated by the failure of many bacteria to respond to conventional antibiotics. Accordingly, the need for effective control of bacterial and virus organisms is assuming greatly increased significance.

In the case of hand and skin disinfection a biocidal agent needs to kill the widest possible range of microorganisms in the least possible time without toxicity, irritation or other hazard and have a long shelf life.

Typical of these biocides are chlorine, iodophors and organic chemicals such as chlorhexidine which are commonly employed in hospitals and surgeries. The most widely accepted form of safe, effective biocide is a solution of chlorhexidine gluconate in aqueous ethanol. A full discussion of this product appears in the paper entitled "Detergents compared with each other and with antiseptics as skin 'degerminating agents'" by H. A. Lily et al in Journal of Hygiene (U.K.). Further technical disclosure of the product appears in Australian Pat. Nos. 157,758 and 222,033. Conventionally, this chlorhexidine solution is commercially supplied in a pump pack or manufactured by the hospital pharmacist as required.

Unfortunately, however, in use known alcohol and chlorhexidine solutions have inherent difficulties including the following:

(1) Openable bottles of alcoholic chlorhexidine are subject to contamination both at the time of fitting the pump head and when the pump is being operated.

(2) The 60-70% aqueous ethanol system is highly flammable. Spillage from the plastic bottle or dispenser at any time could result in a fire.

(3) The mist as applied from pump dispensers is a highly flammable mist. This could be highly dangerous since it is being sprayed directly onto the skin.

(4) The spray mist does not confine itself to the target area, wastage occurs due to overspray.

(5) The alcoholic lotion as sprayed on the skin is difficult to control due to its low viscosity. It tends to run off the skin and evaporate rapidly before being evenly distributed.

(6) The shelf life of pump packs of a volatile fluid such as alcohol is restricted by the fact that the pack is not sealed perfectly and evaporation can occur over a period of time.

(7) The spray or lotion product is messy to use since once one hand has been sprayed it must become contaminated as the pack is held to spray the other hand.

Accordingly, chlorhexidine alcohol solutions must be formulated very carefully to optimize its biocidal performance.

A foamable composition using aqueous chlorhexidine solutions is disclosed in U.S. Defensive publication T943,010. The composition generally utilizes chlorhexidene with more than 50% water at least 10% of ethoxylated alcohols surfactants with thickeners and propellants to form an aerosol foam similar to shaving cream foams.

DESCRIPTION OF THE INVENTION

With the above difficulties in mind, the present invention provides an improved composition containing an aqueous alcoholic chlorhexidine solution in an aerosol form which is easy and safe to use. In this respect, extensive research over several years was necessary on a variety of differing compositions before the viability of an aerosol type became apparant.

Accordingly, a biocidal composition comprising:
(a) from 0.1 to 10% w/w of chlorhexidine;
(b) 70 to 96.9% w/w of a quick breaking alcoholic foaming agent comprising:
  (i) an aliphatic alcohol
  (ii) a fatty alcohol
  (iii) water
  (iv) a surface active agent
(c) from 3 to 20% w/w of an aerosol propellant.

The inclusion of a corrosion inhibitor is only necessary where the composition is stored in metal containers which are typically of tin plate or aluminum to counteract the corrosive nature of chlorhexidine formulations. However, if the container is non metal e.g. glass the inclusion of a corrosion inhibitor is not necessary.

As stated the composition of the invention is an aerosol form. This is most appropriate for a biocide as it avoids or minimizes the conventional defects of contamination and spillage. Pressurized aerosol containers are readily available, have been extensively tested and are well accepted.

PREFERRED FEATURES OF THE INVENTION

In an effort to minimize the aforementioned difficulty of overspray and early evaporation, the aqueous alcoholic chlorhexidine solution is carried by a foaming agent in the present invention, more particularly of a quick break foam variety. This has the ability of providing a thick ball of foam carrier for the alcoholic chlorhexidine solution. The foam disintegrates easily when spread. Thus, proper coverage can be effected to the surface to be cleansed without premature evaporation of the biocidal component. A general discussion of quick break foams can be found in Australian Pat. No. 463,216. In a preferred embodiment of the present invention, a particular quick break foaming agent has been developed which has not been previously disclosed in this context.

The aliphatic alcohol such as methyl alcohol, ethyl alcohol, isopropyl alcohol, butyl alcohol or mixtures thereof is used in amounts from 40-76% w/w composition more preferably 55-70% w/w and most preferably 60% w/w.

Water is used in amounts from 15 to 45% w/w, preferably 20 to 35% w/w.

The fatty alcohol such as cetyl alcohol, stearyl alcohol, lauryl alcohol, myristyl alcohol, palmityl alcohol or mixtures thereof preferably in amounts from 0.5 to 7.5% w/w.

The surface active agent is preferably an ethoxylated surface active agent selected from ethoxylated sorbitan ester such as ethoxylated sorbitan stearate or palmitate, oleate, nonyl phenol ethoxylates and fatty alcohol ethoxylates (as an emulsifier); typically in amounts from 0.1 to 3% w/w.

From the view point of performance aqueous ethanol of approximately 70% w/w ethanol concentration is the best carrier vehicle for chlorhexidine biocidal solutions and this is the preferred form for use in the present foamable biocide composition.

The aqueous chlorhexidine foam disclosed in U.S. Defensive publication T943,010 is much less effective as a biocide than the formulation of this invention. To reformulate the aqueous composition of that disclosure to use an alcohol carrier is not a simple step.

If the water in that prior art foam was simply replaced with ethanol it would not foam but would simply produce a sloppy mess. Further the high concentration of ethoxylated surfactants in this prior art aqueous formulation would be corrosive in conventional aerosol cans.

It is well known that a base formulation of chlorhexidine in aqueous ethanol tends to degrease and dry out the skin when used regularly e.g. use up to 40 times per shift is common in the hospital environment. Thus, an emollient is preferably incorporated into the foamable biocide composition which would help prevent dehydration of the skin without hindering the performance of the chlorhexidine biocidal composition. Emollients which are particularly preferred are lanoline and polyols such as glycerol, propylene glycerol, sorbitol and low molecular weight polymers thereof. Other examples of emollients are vinyl alcohols and polyvinyl pyrollidone.

When considering the preferred requirement for 70% w/w ethanol, it was found that the composition may have an effect on the solubility characteristics of other additive e.g. fatty alcohols, lanolin and organic acid salts. It is believed the other additives react with the chlorhexidine causing it to be, to some extent, either precipitated or inactivated. Nevertheless, such compositions are still found to be useful.

The chlorhexidine component will normally be present in amounts of from 0.1–10% w/w though larger concentration were found to be possible but with deleterious effects on the efficiency of the entire system. Preferred forms of chlorhexidine are as a gluconate, diacetate, hydrochloride or other salts thereof.

Care should be taken to select a propellent most compatible to the entire system and in this respect the propellant is preferably selected from a group comprising propane, butane, dichloro difluoro methane, dichloro tetra fluoro ethane, and octafluoro cyclo butane. As mentioned the propellant should be presenting amounts from 3–20% w/w though preferably from about 5 to 15% w/w.

Where the container is to be employed is metal it is preferable to incorporate a corrosion inhibitor. This became apparent when researching the invention as several working formulations were achieved which however were found to corrode tin plate or aluminum containers at extraordinary rates resulting in short shelf lives. Typical corrosion inhibitors which are effective include organic acid salts preferable corrosion inhibitors include sorbic acid, benzoic acid, sodium benzoate and potassium sorbate.

These inhibitors are preferably present in amounts of from 0.1 to 6% w/w and more preferably for 0.1 to 3% w/w.

Thus, a typical formulation of the present invention is as follows:

|  | % w/w |
| --- | --- |
| Propellant (e.g. propane, butane, dichloro difluoro methane, dichloro tetra fluoro ethane, octafluoro cyclo butane and mixtures thereof) | 3–20 |
| Chlorhexidine (as gluconate, diacetate hydrochloride and mixtures thereof, & other salts) | .1–10 |
| Fatty alcohol (e.g. cetyl alcohol, stearyl alcohol, lauryl alcohol, myristyl alcohol, palmityl alcohol and mixtures thereof) | .5–7.5 |
| Aliphatic alcohol (e.g. methyl alcohol, ethyl alcohol, isopropyl alcohol, butyl alcohol and mixtures thereof) | 40–76 |
| Water | 15–45 |
| Polyol (e.g. glycerol, propylene glycol, sorbitol & low molecular weight polymers thereof) | 1–10 |
| Organic acid salt (e.g. sorbic acid benzoic acid) | .1–6.0 |
| Surface active agent (e.g. ethyoxylated sorbitan stearate, palmitate, oleate, nonyl phenol ethoxylates, fatty alcohol ethoxylates) | .1–3.0 |

| Particularly Preferred Formuations | |
| --- | --- |
| | % w/w |
| Example 1 | |
| Chlorhexidene gluconate 20% | 5.0 |
| Cetyl stearyl alcohol | 2.5 |
| Ethoxylated sorbitan monostearate | 0.5 |
| Propylene glycol | 3.0 |
| Ethyl alcohol (95%) | 57.0 |
| Sodium benzoate | 0.2 |
| Purified water | 22.8 |
| Dichloro difluoro methane ) blend | 9.0 |
| Dichloro tetrafluoro ethane ) | |
| | 100.0 |
| Example 2 | |
| Chlorhexidine diacetate | 1.0 |
| Myristyl alcohol | 3.0 |
| Ethoxylated cetylalchol | 0.8 |
| Glycerol | 2.5 |
| Isopropyl alcohol | 60.0 |
| Potassium sorbate | 0.3 |
| Purified water | 25.4 |
| Butane/propane | 7.0 |
| | 100.0 |
| Example 3 | |
| Chlorhexidine gluconate 20% | 5.0 |
| Myristyl alcohol | 0.8 |
| Ethoxylated Myristyl alcohol | 0.8 |
| Glycerol | 2.5 |
| Ethyl alcohol 95% | 58.0 |
| Potassium sorbate | 1.0 |
| Purified water | 20.3 |
| Dichloro difluoro methane ) | 10.0 |
| Dichloro tetrafluoro ethane ) | |
| | 100.0 |
| Example 4 | |
| Chlorhexidine Acetate | 0.5 |
| Cetyl Stearyl Alcohol | 1.6 |
| Ethoxylated Sorbitan Monostearate | 0.4 |
| Propylene Glycol | 2.0 |
| Ethyl Alcohol 95% | 60.9 |

-continued

Particularly Preferred Formuations

| | % w/w |
|---|---|
| Sodium Benzoate | 1.2 |
| Purified Water | 29.4 |
| Propane/Butane | 4.0 |
| | 100.0 |

Example 5

| | |
|---|---|
| Chlorhexidine Acetate | 0.3 |
| Cetyl Stearyl Alcohol | 3.5 |
| Ethoxylated Sorbitan Monostearate | 0.9 |
| Glycerine | 1.5 |
| Isoproyl Alcohol | 58.2 |
| Potassium Sorbate | 0.5 |
| Purified Water | 28.6 |
| Propane/Butane | 6.5 |
| | 100.0 |

The following are details of tests which were carried out of such formulations in which the formulation is identified by the Trade mark HEXIFOAM.

TEST A

A series of In-vitro tests were performed on "Hexifoam" to determine the efficacy of the Chlorhexidine biocide within the foamable composition.

The tests were designed to establish whether any loss of biocidal activity of the chlorhexidine component was occurring. Comparative evaluations were also performed utilizing "Hexifoam" (without Chlorhexidine) and unformulated non-alcohol Chlorhexidine Gluconate Standard.

The product was evaluated in a suspension test based on the principles outlined in British Standard BS.3286 under the following test conditions.

| | |
|---|---|
| Product Dilutions | 1:2 v/v, 1:4 v/v |
| Contact Time | 1 minute, 2 minutes, 3 minutes, and 5 minutes |
| Organism | *Pseudomonas aeruginosa* NCTC 6749 |
| Organic Challenge | 10% Sheep Serum |
| Inoculum Density | 106–107 orgs/ml. |
| Product Diluent | Distilled Water with 10% Sheep Serum |
| Inactivator | Nutrient Broth No. 2., Lecithin Tween 80 |
| Temperature | Ambient |

Results
Test Organism: *Pseudomonas aeruginosa*

| Sample | Dilution Concentration | Initial Count per ml | Surviving Organisms per ml. | | | |
|---|---|---|---|---|---|---|
| | | | 1 min | 2 min | 3 min | 5 min |
| Hexifoam | 1:2 | 8.0 × 10⁶ | /10 | /10 | /10 | /10 |
| Hexifoam without Chlorhexidine | 1:2 | 8.0 × 10⁶ | /10 | /10 | /10 | /10 |

| | | | 1 min | 2 min | 3 min | |
|---|---|---|---|---|---|---|
| Hexifoam | 1:4¹ | 3.9 × 10⁶ | /10 | /10 | /10 | |
| Hexifoam without Chlorhexidine | 1:4 | 3.9 × 10⁶ | 1,500,000 | 800,000 | 500,000 | |
| Chlorhexidine | 0.25% | 5.0 × 10⁶ | /10 | /10 | /10 | |

Notes:
1. At 1:4 dilution of Hexifoam the concentration of Chlorhexidine is 0.25%
2. '/' indicates less than; Less than 10 is the detection sensitivity of the test method i.e. no surviving organisms detected.

CONCLUSION

The results have indicated that a dilution of the product Hexifoam of 1:4 v/v continues to demonstrate excellent biocidal properties while the base material without chlorhexidine fails to show any significant biocidal properties. This is indicative of little or no loss of activity of the chlorhexidine within the foamable biocide.

The comparative tests with Chlorhexidine Gluconate standard at 0.25% confirmed that the biocidal activity under the above test conditions was found to be equivalent.

The product Hexifoam has shown very rapid biocidal action against the organisms *Pseudomonas aeruginosa* and *Staphylococcus aureus* (Our Ref N 17, 614). Complete kill of the test organisms was achieved within 1 minute in the in-vitro tests performed to date.

TEST B

A sample of "Hexifoam" was received at the laboratory to be evaluated for its biocidal properties against the organism Staphylococcus aureus.

The product was evaluated in a suspension test in accordance with the principles outlined in British Standard BS.3286 under the following test conditions.

| | |
|---|---|
| Product Dilutions | 1:2 v/v |
| Contact Time | 1 minute, 2 minutes, 5 minutes |
| Organism | *Staphylococcus aureus* 4163 |
| Organic Challenge | 10% Sheep Serum |
| Inoculum Density | 106 orgs/ml., |
| Product Diluent | Standard Hard Water-10% Sheep Serum |
| Inactivator | Nutrient Broth No. 2 Lecithin Tween 80 |
| Temperature | Ambient |

| Initial count | Final Count pr ml* | | |
|---|---|---|---|
| | 1 Min. | 2 Mins. | 5 Mins. |
| 2.0 × 10⁶ | Less than 10 | Less than 10 | Less than 10 |

*Results presented are Geometric Means of duplicate tests.

The Kill Factor achieved in all cases was greater than 2.0×a0⁵.

TEST C

The product Hexifoam batch 4073 was evaluated for its biocidal activity using a suspension test based on the principles outlined in British Standard BS.3286 . The results obtained are as follows:

| | |
|---|---|
| Product | Hexifoam |
| Test Organism | *C. albicans* ATCC 10231 |
| Product Dilution | 1:2 w/v |
| Diluent | Distilled water with 10% sheep serum |
| Organic Challenge | 10% sheep serum |
| Temperature | Ambient |
| Contact Time | One minute |
| Inactivator | Nutrient Broth No. 2 (Oxoid) with lecithin and Tween 80. |

| Initial Count | Final Count | Kill Factor | % Kill |
|---|---|---|---|
| 3.7 × 10⁶ | Less than 10 | Greater than 3.7 × 10⁵ | Greater than 99.99973 |

Notes:
1. Results presented are geometric means of duplicate results.
2. Kill factor is defined as the ratio of initial count versus final count.
3. A kill factor of 10⁴ is regarded as significant biocidal activity.

TEST D

The product Hexifoam batch 4073 was evaluated for its biocidal activity using a suspension test based on the principals outlined in British Standard BS.3286. The results obtained are as follows:

| Product | Hexifoam |
|---|---|
| Test Organism | E. coli NCTC 8196 |
| Product Dilution | 1:2 w/v |
| Diluent | Distilled water with 10% sheep serum |
| Organic Challenge | 10% sheep serum |
| Temperature | Ambient |
| Contact Time | One minute |
| Inactivator | Nutrient Broth No. 2 (Oxoid) with lecithin and Tween 80. |

| Initial Count orgs/ml | Final Count orgs/ml | Kill Factor | % Kill |
|---|---|---|---|
| $6.7 \times 10^6$ | Less than 10 | Greater than $6.7 \times 10^5$ | Greater than 99.99986 |

Notes:
1. Results presented are geometric means of duplicate results.
2. Kill factor is defined as the ratio of initial count versus final count.
3. A kill factor of $10^4$ is regarded as significant biocidal activity.

TEST E

The product Hexifoam batch 4073 was evaluated for its biocidal activity using a suspension test based on the principles outlined in British Standard BS.3286. The results obtained are as follows:

| Product | Hexifoam |
|---|---|
| Test Organism | S. typhimurium (clinical isolate) |
| Product Dilution | 1:2 w/v |
| Diluent | Distilled water with 10% sheep serum |
| Organic Challenge | 10% sheep serum |
| Temperature | Ambient |
| Contact Time | One minute |
| Inactivator | Nutrient Broth No. 2 (Oxoid) with lecithin and Tween 80. |

| Initial Count orgs/ml | Final Count orgs/ml | Kill Factor | % Kill |
|---|---|---|---|
| $6.7 \times 10^6$ | Less than 10 | Greater than $6.7 \times 10^5$ | Greater than 99.99986 |

Notes:
1. Results presented are geometric means of duplicate results.
2. Kill factor is defined as the ratio of initial count versus final count.
3. A kill factor of $10^4$ is regarded as significant biocidal activity.

TEST F

The product Hexifoam batch 4073 was evaluated for its biocidal activity using a suspension test based on the principles oulined in British Standard BS.3286. The results obtained are as follows:

| Product | Hexifoam |
|---|---|
| Test Organism | S. aureus (Methicillan Resistant, Clinical Isolate) |
| Product Dilution | 1:2 w/v |
| Diluent | Sterile Distilled water with 10% sheep serum |
| Organic Challenge | 10% sheep serum |
| Temperature | Ambient |
| Contact Time | One minute |
| Inactivator | Nutrient Broth No. 2 (Oxoid) with lecithin and Tween 80. |

| Initial Count orgs/ml | Final Count orgs/ml | Kill Factor | % Kill |
|---|---|---|---|
| $4.6 \times 10^6$ | Less than 10 | Greater than $4.6 \times 10^5$ | Greater than 99.9954% |

Notes:
1. Results presented are geometric means of duplicate results.
2. Kill factor is defined as the ratio of initial count versus final count.
3. A kill factor of $10^4$ is regarded as significant biocidal activity.

TEST G

The product Hexifoam batch 4073 was evaluated for its biocidal activity using a suspension test based on the principles outlined in British Standard BS.3286. The results obtained are as follows:

| Product | Hexifoam |
|---|---|
| Test Organism | T. rubrum, (clinical isolate) |
| Product Dilution | 1:2 w/v |
| Diluent | Distilled water with 10% sheep serum |
| Organic Challenge | 10% sheep serum |
| Temperature | Ambient |
| Contact Time | 5 minutes |
| Inactivator | Nutrient Broth No. 2 (Oxoid) with lecithin and Tween 80. |

| Initial Count orgs/ml | Final Count orgs/ml | Kill Factor | % Kill |
|---|---|---|---|
| $1.0 \times 10^7$ | Less than 10 | Greater than $1.0 \times 10^6$ | Greater than 99.9999 |

Notes:
1. Results presented are geometric means of duplicate results.
2. Kill factor is defined as the ratio of initial count versus final count.

TEST H

Hexifoam was evaluated in our laboratory in a short preliminary in-vitro trial using various dosages and exposure times against *Pseudomonas aeruginosa* NCTC 6749.

EXPERIMENTAL DESIGN

Two volunteers from our laboratory were used. For the duration of the experiment the hands of the personnel were allowed to be washed only with traditional bar soap. No chlorhexidine based products such as our standard laboratory soap were used to avoid a build up of chlorhexidine on the skin. The time interval between Hexifoam trials was at least three days.

Fresh 24 hour suspension cultures of *P. aeruginosa* NCTC 6749 were utilized for each trial. Cultures were grown in Wright and Mundy broth (DiFco) for 24 hours at 37° C.

One ml. of *P. aeruginosa* representing at least $1 \times 10^9$ cells was applied to the palm of one hand. This was then carefully rubbed over the surface of both hands. No culture was allowed to be dropped from the hands during this operation. If so the trial was declared void at that time. The person washed their hands and the inoculation was repeated after a break of at least two hours. The culture was allowed to dry completely on the hands before application of Hexifoam.

Hexifoam was weighed on to a plastic square and then applied to the hands. This procedure ensured accurate dosage by weight. The Hexifoam was rubbed over the entire surface of the hands. Exposure time was monitored with a stop watch. At the end of the allocated exposure time the hands were placed into 500 ml. of inactivator solution comprising 3% Tween 80, 2% lecithin. For one minute the hands were scrubbed in the inactivator solution to release any surviving *P. aeruginosa* into the liquid.

| Trial Description | Weight of Hexifoam Used (g) | Exposure Time (sec) |
|---|---|---|
| Recovery Control | 0 | 0 |
| Test 1 | 1 | 30 |
| Test 2 | 2 | 30 |

-continued

| | | |
|---|---|---|
| Test 3 | 2 | 60 |

Results Recovery Control

| Culture Count onto Hands Total Cells | Control Recovery Total Cells Volunteer | | % Recovery Volunteer | | Geometric Mean % Recovery |
|---|---|---|---|---|---|
| | 1 | 2 | 1 | 2 | |
| $2.8 \times 10^9$ | $5.5 \times 10^6$ | $21.0 \times 10^6$ | 0.196 | 0.750 | 0.384 |

0.384% is used to calculate the expected recovery in all Hexifoam trials. This adjusts for culture variation and is needed to calculate reductions achieved.

Hexifoam Trials

| Trial Description | Culture Count onto Hands Total Cells (y) | Recovery Total Cells Volunteer | |
|---|---|---|---|
| | | 1 | 2 |
| 1 g 30 Sec | $3.1 \times 10^9$ | $1.3 \times 10^6$ | $3.2 \times 10^6$ |
| 2 g 30 Sec | $2.6 \times 10^9$ | $5.0 \times 10^5$ | $5.5 \times 10^5$ |
| 2 g 60 Sec | $4.3 \times 10^9$ | $2.55 \times 10^4$ | $11.5 \times 10^4$ |

| Trial Description | Geometric Mean Recovery | Calculated Recovery 0.384% x y | Mean Log Reduction | Kill |
|---|---|---|---|---|
| 1 g 30 Sec | $2.03 \times 10^6$ | $11.9 \times 10^6$ | 0.768 | 82.95 |
| 2 g 30 Sec | $5.24 \times 10^5$ | $10.0 \times 10^6$ | 1.281 | 94.76 |
| 2 g 60 Sec | $5.4 \times 10^4$ | $16.5 \times 10^6$ | 2.485 | 99.67 |

The foamable compositions within the present invention improve over prior chlorhexidine biocide products commercially available as follows:

(1) As a pressurized aerosol the pack cannot become internally contaminated.

(2) The aerosol cannot spill and therefore represents no fire hazard.

(3) The foam, as dispensed, is very hard to ignite and will not readily burn as does a spray, presenting a much reduced hazard.

(4) The foam is easily handled and does not allow any waste due to overspray.

(5) The foam as developed is of a fast breaking variety. When applied to the skin it is a stable lump, but body heat or friction cause it to melt and spread onto the skin in a unique, controllable, and fast dispersing manner.

(6) The shelf life of the aerosol is good and with some formulations is probably in excess of five years almost irrespective of the storage environment.

(7) Since a ball of foam can be held in one hand the pack only needs to be touched once and the treated hands never need to come into contact with it.

Quite unexpectedly, having regard to the prior research carried out, the stated combination has in testing exceeded performance expectation. Further, as disclosed initial microbiological tests have shown the biocidal compositions retain the full broad spectrum of activity of chlorhexidine and to be surprisingly fast acting; killing 99% plus of M.R.S.A. (Methicillan Resistant *S. Aureus*) in less than sixty seconds. This result is clearly superior to conventional chlorhexidine compositions.

The claims defining the invention are as follows:

1. A biocidal foam aerosol composition stored in a corrosion resistant pressurized aerosol container comprising:
   (a) from 0.1 to 10% w/w of chlorhexidine;
   (b) 70 to 96% w/w of a quick breaking alcoholic foaming agent comprising:
      (i) an aliphatic alcohol selected from the group consisting of methanol, ethanol, isopropanol and butanol;
      (ii) a fatty alcohol selected from the group consisting of cetyl alcohol, lauryl alcohol, myristyl alcohol and palmityl alcohol;
      (iii) water;
      (iv) an ethoxylated surface active agent;
   (c) from 3 to 20% w/w of a aerosol propellant selected from the group consisting of propane, butane, dichloro difluoro methane, dichloro tetra fluoro ethane and octafluoro cyclo butane.

2. The composition as claimed in claim 1 wherein the chlorhexidine is selected from a gluconate, diacetate or hydrochloride.

3. The composition of claim 1 wherein the aliphatic alcohol is present in amounts from 40 to 76% w/w; the fatty alcohol is present in amounts from 0.5 to 7.5% w/w; water is present in amounts from 15 to 45% w/w; and the surfactant is present in amounts from 0.1 to 3% w/w.

4. The composition of claim 1 wherein the ethoxylated surface active agent is selected from the group consisting of ethoxylated sorbitan stearate, palmitate, oleate, nonyl phenol ethoxylates and fatty alcohol ethoxylates.

5. The composition of claim 1 further including an emollient.

6. The composition of claim 5 wherein the emollient is selected from the group consisting of lanolin, vinyl alcohol, polyvinyl pyrollidone and polyols selected from the group consisting of glycerol, propylene glycol, and sorbitol.

* * * * *